(12) United States Patent
Bakhru et al.

(10) Patent No.: US 10,534,006 B2
(45) Date of Patent: Jan. 14, 2020

(54) MICROFLUIDIC CHIP-BASED, UNIVERSAL COAGULATION ASSAY

(71) Applicant: Perosphere Technologies Inc., Danbury, CT (US)

(72) Inventors: Sasha Bakhru, Providence, RI (US); Bryan Laulicht, Danbury, CT (US); Stefan Zappe, Danbury, CT (US); Solomon Steiner, Mount Kisco, NY (US)

(73) Assignee: Perosphere Technologies Inc., Danbury, CT (US)

( * ) Notice: Subject to any disclaimer, the term of this patent is extended or adjusted under 35 U.S.C. 154(b) by 0 days.

(21) Appl. No.: 15/909,677

(22) Filed: Mar. 1, 2018

(65) Prior Publication Data
US 2018/0252734 A1 Sep. 6, 2018

Related U.S. Application Data

(63) Continuation of application No. 14/849,348, filed on Sep. 9, 2015, now Pat. No. 9,910,053.
(Continued)

(51) Int. Cl.
*G01N 33/86* (2006.01)
*G01N 33/49* (2006.01)
(Continued)

(52) U.S. Cl.
CPC ........ *G01N 33/86* (2013.01); *B01L 3/502715* (2013.01); *B01L 9/527* (2013.01);
(Continued)

(58) Field of Classification Search
CPC .................................................. G01N 33/86
See application file for complete search history.

(56) References Cited

U.S. PATENT DOCUMENTS 5,039,617 A * 8/1991 McDonald ......... G01N 33/4905
422/417
5,089,415 A * 2/1992 La Duca ................ G01N 33/86
210/632
(Continued)

FOREIGN PATENT DOCUMENTS

EP 1324395 7/2003
JP 2013-257154 A 12/2013
(Continued)

OTHER PUBLICATIONS

Berney and O\riordan, "Impedance measurement monitors blood coagulation", Analog Dialogue 42-08:1-3 (2008).
(Continued)

*Primary Examiner* — Lyle Alexander
*Assistant Examiner* — Dwan A Gerido
(74) *Attorney, Agent, or Firm* — Pabst Patent Group LLP

(57) ABSTRACT

A microfluidic, chip-based assay device has been developed for measuring physical properties of an analyte (particularly, whole blood or whole blood derivatives). The technologies can be applied to measure clotting times of whole blood or blood derivatives, determine the effects of anticoagulant drugs on the kinetics of clotting/coagulation, as well as evaluate the effect of anticoagulant reversal agents. These technologies can additionally be used to optimize the dosage of anticoagulation drugs and/or their reversal agents. The assay is independent of the presence of anticoagulant; clotting is activated by exposure of the blood sample in the device to a glass (or other negatively charged material such as oxidized silicon) surface, which activates the intrinsic pathway and can be further hastened by the application of shear flow across the activating materials surface. The absence of chemical activating agents and highly controlled (Continued)

and reproducible micro-environment yields a point of care universal clotting assay.

17 Claims, 14 Drawing Sheets

Related U.S. Application Data

(60) Provisional application No. 62/048,183, filed on Sep. 9, 2014.

(51) Int. Cl.
*B01L 3/00* (2006.01)
*B01L 9/00* (2006.01)

(52) U.S. Cl.
CPC .. *G01N 33/4905* (2013.01); *B01L 2300/0645* (2013.01); *B01L 2300/0681* (2013.01); *B01L 2300/0816* (2013.01); *B01L 2300/1827* (2013.01)

(56) References Cited

U.S. PATENT DOCUMENTS

| | | | | |
|---|---|---|---|---|
| 5,167,145 | A | 12/1992 | Butler | G01N 33/4905 250/341.5 |
| 5,372,946 | A * | 12/1994 | Cusak | G01N 33/4905 356/246 |
| 6,437,551 | B1 * | 8/2002 | Krulevitch | G01N 33/5438 324/649 |
| 7,005,857 | B2 | 2/2006 | Stiene | |
| 7,291,310 | B2 | 11/2007 | Martin | |
| 7,821,620 | B2 | 10/2010 | Dogariu | |
| 8,512,648 | B2 | 8/2013 | Bau-Madsen | |
| 8,772,039 | B2 | 7/2014 | Nadkarni | |
| 8,828,320 | B2 | 9/2014 | Bardell | |
| 9,297,816 | B1 | 3/2016 | Pyayt | |
| 9,910,053 | B2 * | 3/2018 | Bakhru | G01N 33/4905 |
| 1,006,094 | A1 | 8/2018 | Micheels | |
| 2003/0064414 | A1 * | 4/2003 | Benecky | C12Q 1/56 435/7.21 |
| 2004/0072357 | A1 | 4/2004 | Stiene | A61B 5/1473 324/449 |
| 2005/0015001 | A1 | 1/2005 | Lac | A61B 8/12 600/369 |
| 2005/0129580 | A1 * | 6/2005 | Swinehart | B01F 5/0475 422/400 |
| 2005/0249633 | A1 | 11/2005 | Blatt | B01L 3/5027 422/400 |
| 2006/0062696 | A1 * | 3/2006 | Chow | B01L 3/502746 422/400 |
| 2008/0129736 | A1 * | 6/2008 | Sun | C12Q 1/686 345/442 |
| 2009/0221011 | A1 * | 9/2009 | Stiene | B01L 3/502715 435/13 |
| 2010/0248278 | A1 | 9/2010 | Pouteau | |
| 2011/0024309 | A1 | 2/2011 | Lee | |
| 2011/0223627 | A1 | 9/2011 | Neeves | |
| 2012/0107851 | A1 * | 5/2012 | Killard | B01L 3/502753 435/13 |
| 2013/0192349 | A1 | 8/2013 | Ramkumar et al. | |
| 2014/0270458 | A1 * | 9/2014 | Smith | G01N 33/5094 382/134 |
| 2014/0273064 | A1 * | 9/2014 | Smith | G01N 33/5017 435/29 |
| 2015/0305681 | A1 | 10/2015 | Nadkarni | |
| 2015/0316533 | A1 | 11/2015 | Kerimo | |

FOREIGN PATENT DOCUMENTS

| | | |
|---|---|---|
| WO | 2004093641 | 11/2004 |
| WO | 2011075614 | 6/2011 |
| WO | 2014085804 | 6/2014 |

OTHER PUBLICATIONS

Kallensperger, et al., "Technical Note: Patterning of platinum (Pt) thin films by chemical wet etching in Aqua Regia", J Micromech Microeng, 32(6):67001 (2012).

Office Action dated Mar. 27, 2018, mailed in the Japanese Patent Application No. 2017-513081, the Japanese National Phase Entry Application of PCT/US2015/049198.

* cited by examiner

Closed version

Open version

Closed version

Open version

Closeups of front side features

Closeups of backside features

MICROFLUIDIC CHIP-BASED, UNIVERSAL COAGULATION ASSAY

CROSS REFERENCE TO RELATED APPLICATION

This application is a continuation of U.S. application Ser. No. 14/849,348, filed Sep. 9, 2015, and issued as U.S. Pat. No. 9,910,053, which claims benefit of and priority to U.S. Provisional Application No. 62/048,183, filed Sep. 9, 2014, all of which are herein incorporated in their entirety by reference.

FIELD OF THE INVENTION

The present invention relates to a point of care microfluidic chip-based universal coagulation assay device and reader that can be used to measure the global coagulation status of normal healthy, coagulation impaired, anticoagulated, and anticoagulant reversed patients.

BACKGROUND OF THE INVENTION

Coagulation (clotting) is the process by which blood changes from a liquid to a gel. It potentially results in hemostasis, the cessation of blood loss from a damaged vessel, followed by repair. The mechanism of coagulation involves activation, adhesion, and aggregation of platelets along with conversion of fibrinogen to fibrin, which deposits and matures into a robust network. Disorders of coagulation are disease states which can result in bleeding or obstructive clotting (thrombosis).

Coagulation begins very quickly after an injury to the blood vessel has damaged the endothelium lining the vessel. Exposure of blood to the space under the endothelium initiates two categories of processes: changes in platelets, and the exposure of subendothilial tissue factor to plasma Factor VII, which ultimately leads to fibrin formation. Platelets immediately form a plug at the site of injury; this is called primary hemostasis. Secondary hemostasis occurs simultaneously: additional coagulation factors or clotting factors beyond Factor VII, respond in a complex cascade to form fibrin strands, which strengthen the platelet plug.

The coagulation cascade of secondary hemostasis has two pathways which lead to fibrin formation. These are the contact activation pathway (also known as the intrinsic pathway), and the tissue factor pathway (also known as the extrinsic pathway). It was previously thought that the coagulation cascade consisted of two pathways of equal importance joined to a common pathway. It is now known that the primary pathway for the initiation of blood coagulation is the tissue factor pathway. The pathways are a series of reactions, in which a zymogen (inactive enzyme precursor) of a serine protease and its glycoprotein co-factor are activated to become active components that then catalyze the next reaction in the cascade, ultimately resulting in cross-linked fibrin. Coagulation factors are generally indicated by Roman numerals, with a lowercase "a" appended to indicate an active form.

The coagulation factors are generally serine proteases which act by cleaving downstream proteins. There are some exceptions. For example, FVIII and FV are glycoproteins, and Factor XIII is a transglutaminase. The coagulation factors circulate as inactive zymogens. The coagulation cascade is classically divided into three pathways. The tissue factor and contact activation pathways both activate the "final common pathway" of factor X, thrombin and fibrin.

Tissue Factor Pathway (Extrinsic)

The main role of the tissue factor pathway is to generate a "thrombin burst", a process by which thrombin, the most important constituent of the coagulation cascade in terms of its feedback activation roles, is released very rapidly. FVIIa circulates in a higher amount than any other activated coagulation factor. The process includes the following steps:

Following damage to the blood vessel, FVII leaves the circulation and comes into contact with tissue factor (TF) expressed on tissue-factor-bearing cells (stromal fibroblasts and leukocytes), forming an activated complex (TF-FVIIa).

TF-FVIIa activates FIX and FX.

FVII is itself activated by thrombin, FXIa, FXII and FXa.

The activation of FX (to form FXa) by TF-FVIIa is almost immediately inhibited by tissue factor pathway inhibitor (TFPI).

FXa and its co-factor FVa form the prothrombinase complex, which activates prothrombin to thrombin.

Thrombin then activates other components of the coagulation cascade, including FV and FVIII (which activates FXI, which, in turn, activates FIX), and activates and releases FVIII from being bound to vWF.

FVIIIa is the co-factor of FIXa, and together they form the "tenase" complex, which activates FX; and so the cycle continues. ("Tenase" is a contraction of "ten" and the suffix "-ase" used for enzymes.)

Contact Activation Pathway (Intrinsic)

The contact activation pathway begins with formation of the primary complex on collagen by high-molecular-weight kininogen (HMWK), prekallikrein, and FXII (Hageman factor). Prekallikrein is converted to kallikrein and FXII becomes FXIIa. FXIIa converts FXI into FXIa. Factor XIa activates FIX, which with its co-factor FVIIIa form the tenase complex, which activates FX to FXa. The minor role that the contact activation pathway has in initiating clot formation can be illustrated by the fact that patients with severe deficiencies of FXII, HMWK, and prekallikrein do not have a bleeding disorder. Instead, contact activation system seems to be more involved in inflammation.

Coagulation Assays

Several techniques, including clot-based tests, chromogenic or color assays, direct chemical measurements, and ELISAs, are used for coagulation testing. Of these techniques, clot-based and chromogenic assays are used most often, Whereas clotting assays provide a global assessment of coagulation function, chromogenic tests are designed to measure the level or function of specific factors.

Clot-based assays are often used for evaluation of patients with suspected bleeding abnormalities and to monitor anticoagulant therapy. Most of these tests use citrated plasma, which requires tens of minutes for preparation and typically requires hours to days to receive results in a hospital setting. The end point for most clotting assays is fibrin clot formation.

Prothrombin Time (PT) is performed by adding a thromboplastin reagent that contains tissue factor (which can be recombinant in origin or derived from an extract of brain, lung, or placenta) and calcium to plasma and measuring the clotting time. The PT varies with reagent and coagulometer but typically ranges between 10 and 14 seconds. The PT is prolonged with deficiencies of factors VII, X, and V, prothrombin, or fibrinogen and by antibodies directed against these factors. This test also is abnormal in patients with inhibitors of the fibrinogen-to-fibrin reaction, including high doses of heparin and the presence of fibrin degradation products. Typically, PT reagents contain excess phospholipid so that nonspecific inhibitors (i.e., lupus anticoagulants), which react with anionic phospholipids, do not prolong the clotting time. The PT is most frequently used to monitor warfarin therapy. PT measurements are not comparable between devices or centers and most warfarin clinics develop their own normal patient range, which is non-transferrable and highly specific to the exact reagents present in the specific assay used.

The activated Partial Thromboplastin Time (aPTT) assay is performed by first adding a surface activator (e.g., kaolin, celite, ellagic acid, or silica) and diluted phospholipid (e.g., cephalin) to citrated plasma. At the point of care, aPTT can also be measured in whole blood typically using similar chemical activating agents. The phospholipid in this assay is called partial thromboplastin because tissue factor is absent. After incubation to allow optimal activation of contact factors (factor XII, factor XI, prekallikrein, and high-molecular-weight kininogen), calcium is then added, and the clotting time is measured. aPTT measurements are not comparable between devices or hospitals and most clinical laboratories develop their own normal patient range, which is non-transferrable and highly specific to the exact reagents present in the specific assay used.

Although the clotting time varies according to the reagent and coagulometer used, the aPTT typically ranges between 22 and 40 seconds. The aPTT' may be prolonged with deficiencies of contact factors; factors IX, VIII, X, or V; prothrombin; or fibrinogen. Specific factor inhibitors, as well as nonspecific inhibitors, may also prolong the aPTT. Fibrin degradation products and anticoagulants (e.g., heparin, direct thrombin inhibitors, or warfarin) also prolong the aPTT, although the aPTT is less sensitive to warfarin than is the PT.

The thrombin clotting time (TCT) is performed by adding excess thrombin to plasma. The TCT is prolonged in patients with low fibrinogen levels or dysfibrinogenemia and in those with elevated fibrin degradation product levels. These abnormalities are commonly seen with disseminated intravascular coagulation. The TCT is also prolonged by heparin and direct thrombin inhibitors.

The activated clotting time (ACT) is a point-of-care whole-blood clotting test used to monitor high-dose heparin therapy or treatment with bivalirudin. The dose of heparin or bivalirudin required in these settings is beyond the range that can be measured with the aPTT. Typically, whole blood is collected into a tube or cartridge containing a coagulation activator (e.g., celite, kaolin, or glass particles) and a magnetic stir bar, and the time taken for the blood to clot is then measured. The reference value for the ACT ranges between 70 and 180 seconds. The desirable range for anticoagulation depends on the indication and the test method used. The ACT does not correlate well with other coagulation tests.

For the ecarin clotting time (ECT), venom from the *Echis carinatus* snake is used to convert prothrombin to meizothrombin, a prothrombin intermediate that is sensitive to inhibition by direct thrombin inhibitors. The ECT cannot be used to detect states of disturbed coagulation and is useful only for therapeutic drug monitoring. This assay is insensitive to heparin because steric hindrance prevents the heparin-antithrombin complex from inhibiting meizothrombin. Because ecarin also activates the noncarboxylated prothrombin found in plasma of warfarin-treated patients, levels of direct thrombin inhibitors can be assayed even with concomitant warfarin treatment. Although the ECT has been used in preclinical research, the test has yet to be standardized and is not widely available.

Anti-factor Xa assays are used to measure levels of heparin and low-molecular-weight heparin (LMWH). These are chromogenic assays that use a factor Xa substrate onto which a chromophore has been linked. Factor Xa cleaves the chromogenic substrate, releasing a colored compound that can be detected with a spectrophotometer and is directly proportional to the amount of factor Xa present. When a known amount of factor Xa is added to plasma containing heparin (or LMWH), the heparin enhances factor Xa inhibition by antithrombin rendering less factor Xa available to cleave the substrate. By correlating this result with a standard curve produced with known amounts of heparin, we can calculate the heparin concentration in the plasma. The use of anti-Xa assays requires the knowledge of which anticoagulant the patient is taking in order to use the appropriate calibrator and cannot be used to monitor anti-IIa anticoagulant therapies.

Anticoagulant drugs in clinical use include warfarin, heparins (unfractionated heparin and LMWH), and direct thrombin inhibitors (bivalirudin, hirudin, and argatroban).

Warfarin is effective for primary and secondary prevention of venous thromboembolism; for prevention of cardioembolic events in patients with atrial fibrillation or prosthetic heart valves; for prevention of stroke, recurrent infarction, or cardiovascular death in patients with acute myocardial infarction; and for the primary prevention of acute myocardial infarction in high-risk men. Because of the variability in the anticoagulant response to warfarin, which reflects genetic variations in metabolism and environmental factors such as medications, diet, and concomitant illness, regular coagulation monitoring and dosage adjustment are required to maintain the International Normalized Ratio (INR) within the therapeutic range. Heparins are indirect anticoagulants that activate antithrombin and promote its capacity to inactivate thrombin and factor Xa. To catalyze thrombin inhibition, heparin binds both to antithrombin via a high-affinity pentasaccharide sequence and to thrombin. In contrast, to promote factor Xa inhibition, heparin needs only to bind to antithrombin via its pentasaccharide sequence. Heparin molecules containing <18 saccharide units are too short to bind to both thrombin and antithrombin and therefore cannot catalyze thrombin inhibition. However, these shorter heparin fragments can catalyze factor Xa inhibition, provided that they contain the pentasaccharide sequence. The anticoagulant response to heparin is unpredictable because of variable nonspecific binding to endothelial cells, monocytes, and plasma proteins. Because of this variable anticoagulant response, coagulation monitoring is routinely performed when heparin is given in greater than prophylactic doses. The aPTT is the test most often used to monitor heparin. Unfortunately, aPTT reagents vary in their responsiveness to heparin, and the aPTT therapeutic range differs, depending on the sensitivity of the reagent and the coagulometer used for the test. The aPTT has proved more difficult to standardize than the PT, and the commonly quoted therapeutic range of 1.5 to 2.5 times the control value often leads to systematic administration of subtherapeutic heparin doses. The evidence supporting the concept of an aPTT therapeutic range that predicts efficacy and safety (with respect to bleeding) is somewhat tenuous. Approximately 25% of patients require doses of heparin of >35 000 UM to obtain a therapeutic aPTT and are called heparin resistant. Most of these patients have therapeutic heparin levels when measured with the anti-Xa assay, and the discrepancy between the 2 tests is the result of high concentrations of procoagulants such as fibrinogen and factor VIII, which shorten the aPTT. Although the aPTT response is linear with heparin levels within the therapeutic range, the aPTT becomes immeasurable with higher heparin doses. Thus, a less sensitive test of global anticoagulation such as the ACT is used to monitor the level of anticoagulation in patients undergoing percutaneous coronary interventions or aortocoronary bypass surgery.

LMWH is derived from unfractionated heparin by chemical or enzymatic depolymerization. LMWH has gradually replaced heparin for most indications. LMWH is typically administered in fixed doses when given for prophylactic purposes or in weight-adjusted doses when given for treatment. Pitfalls in the monitoring of LMWH by anti-factor Xa levels include poor comparability between commercially available anti-Xa chromogenic assays, differences in ratios of anti-Xa to anti-IIa among the various LMWH preparations, and the importance of timing of blood sampling in relation to dosing. Although the aPTT may be prolonged with high doses of LMWH, this assay is not used for monitoring. No clinically available point of care assay to date is available for the monitoring of the millions of patients administered LMWH.

Direct thrombin inhibitors bind directly to thrombin and block the interaction of thrombin with its substrates. Three parenteral direct thrombin inhibitors have been licensed for limited indications in North America. Hirudin and argatroban are approved for treatment of patients with heparin-induced thrombocytopenia, whereas bivalirudin is licensed as an alternative to heparin in patients undergoing percutaneous coronary intervention (PCI). Hirudin and argatroban require routine monitoring. The TCT is too sensitive to small amounts of hirudin and argatroban to be used for this purpose. Although the ACT has been used to monitor the higher doses of direct thrombin inhibitors required in interventional settings, it does not provide an optimal linear response at high concentrations. The aPTT is recommended for therapeutic monitoring; however, each direct thrombin inhibitor has its own dose response, and the sensitivity of the test to drug levels varies between aPTT reagents. When hirudin therapy is monitored with the aPTT, the dose is adjusted to maintain an aPTT that is 1.5 to 2.5 times the control, whereas for argatroban, the target aPTT is 1.5 to 3 times control (but not to exceed 100 seconds). The aPTT appears less useful in patients requiring higher doses of direct thrombin inhibitor in cardiopulmonary bypass procedures because this test becomes less responsive at increasing drug concentrations. The ECT appears to be useful for both low and high concentrations of direct thrombin inhibitors and is less affected by interfering substances than the aPTT. However, as stated above, it is not routinely available. The responsiveness of the INR to different drug concentrations differs with assay reagent and with the type of direct thrombin inhibitor. This feature complicates the transitioning of patients with heparin-induced thrombocytopenia from argatroban to vitamin K antagonists.

As is clear from the foregoing, clotting, and inhibition of clotting, is a complex process. The type of anticoagulant can give misleading and dangerous results if determined using the wrong clotting assay. This creates a potentially disastrous scenario when an anticoagulated patient arrives at an emergency room without information as to medicines he is on, as well as the condition being treated. Sometimes it is impossible to wait for further diagnostics to determine the anticoagulant or disorder causing prolonged bleeding. The need for a rapid, accurate, and universal test for clotting, especially a point of care ("POC") test, is well known; options, however, are extremely limited.

It is therefore an object of the present invention to provide a rapid, accurate and universal test for clotting.

It is a further object of the present invention to provide a point of care test for clotting.

It is a still further object of the present invention to provide a test that is accurate, reproducible, easy to operate, and requires a very small amount of sample.

SUMMARY OF THE INVENTION

A microfluidic, chip-based assay device has been developed for measuring physical properties of an analyte (in particular, whole blood or whole blood derivatives). The technologies can in particular be applied to measure clotting times of whole blood or blood derivatives, to determine the effects of anticoagulant drugs on the kinetics of clotting/coagulation, as well as to evaluate the effect of anticoagulant reversal agents. These technologies can additionally be used to optimize the dosage of anticoagulation drugs and/or their reversal agents. The assay is independent of the presence of anticoagulant since clotting is activated by exposure of the blood sample in the device to a glass (or other negatively charged material such as oxidized silicon) surface, which activates the intrinsic pathway and can be further hastened by the application of shear flow across the activating materials surface. The absence of chemical activating agents and highly controlled and reproducible micro-environment yields a point of care universal clotting assay.

The sample is handled in a microfluidic system. The volume of sample introduced into the testing chamber is in the nano-, micro-, or milliliter range (most preferably 1-10 microliters). The sample is introduced into the collection well directly from a blood sample or the individual (such as from a finger stick). In one embodiment, the sample, such as blood or plasma, is collected and transferred to the heated microdevice immediately after collection by syringe into a no-additive red-topped tube or capillary tube. Clotting in the samples, preferably in duplicate, is initiated by exposure of the blood or plasma to the glass surface within the device and the sample exposed to means for analysis of clotting. The blood sample is then drawn from the collection well into the testing chamber either passively by capillary action or with a pump, which induces sheer and exposes the blood sample to the activating materials surface, while delivering a geometrically controlled amount of the blood sample into the testing chamber. The microfluidic system along with integrated electrodes, heater structures or other parts of sensors or actuators is designed to be disposable. The microfluidic system is inserted into an analytical re-usable housing (referred to herein as a "reader") that is part of an analysis instrument, which connects the microfluidic system and provides fluidic, electrical, optical and thermal interfaces for measuring clotting and transmitting the time and characteristics of the measurement to an external reader, monitor, or recorder.

Clotting is assessed by a change in viscosity, optical transmission, electrical impedance, and/or pressure. In the preferred embodiment, clotting is detected through measurement of blood impedance through integrated electrodes and/or through measurement of optical transmission using infrared (IR) LEDs and photodiodes, respectively. An integrated thermal resistive heater/cooler structure such as a solid state heat pump or Peltier cooler keeps the blood sample at a defined temperature, most preferably approximately 37° C. (body temperature), and ensures repeatability and comparability of measurements. As fibrinogen converts to fibrin, the IR absorbance increases until it peaks in a measurable fashion. The determination of whole blood clotting time is made on or about the peak of IR absorbance.

After completion of measurements, the microfluidic chip containing the blood sample is removed from the reader and discarded.

The development of clotting can be monitored by measuring electrical impedance. The development of fibrin increases electrical impedance until it peaks in a measurable fashion. On or about the peak of electrical impedance, the determination of whole blood clotting time is made. Whole blood clotting time can be measured by IR absorption and electrical impedance measured alone or simultaneously as a basis of comparison. The electrical impedance and IR absorption curves are essentially coincident, and provide confirmation via independent measurement modes.

The microfluidic system is fabricated through application of microtechnologies and processing and bonding of wafers made of silicon, glass or other suitable materials. The microfluidic system can also be fabricated through alternative means, for example, through application of soft lithography technologies or through generation of reader parts (made, for example, of plastic or a different suitable, substantially IR-opaque material) that may be used alone or in combination with micropatterned chips to form a microfluidic system. The microfluidic system typically consists of an inlet, an outlet and one or more chambers that are connected through channels, which range in length from tens of microns to millimeters, with heights and depths in the tens of microns to hundreds of microns range.

DETAILED DESCRIPTION OF THE INVENTION

I. Definitions

Microfluidics

Figure 1:
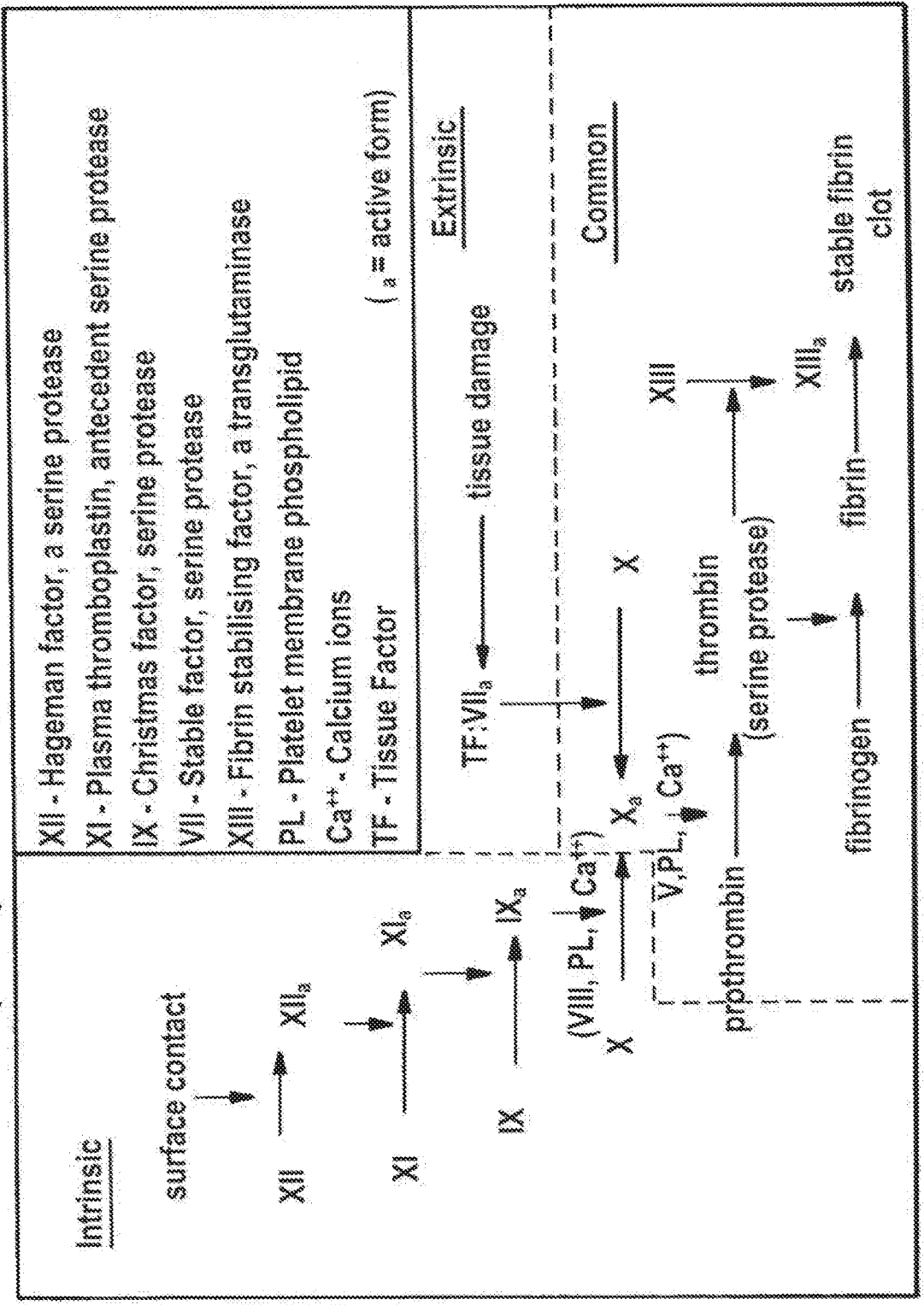
FIG. 1 is a schematic of the coagulation cascade.

Microfluidics is a highly interdisciplinary field, drawing from engineering, physics, chemistry, biochemistry, micro-/nanotechnology, and biotechnology. Small volumes of liquid, ranging from femto- to milliliters are typically handled in a microfluidic system. The methods for fabrication of a microfluidic system typically allow for integration of sensors and/or actuators, so that liquids can be effectively transported, manipulated and analyzed inside the microfluidic system. Interfaces between the microfluidic system and its environment enable implementation of external mechanisms for transport, manipulation and analysis.

Micro-/Nanotechnologies

Micro-/Nanotechnologies are typically used to fabricate microsystems, including microfluidic systems. Micro-/nanotechnologies typically enable generation of structures with dimensions in the micro—or nanometer range. Such technologies can be based on silicon wafer processing technologies, originally developed for fabrication of integrated electronic circuits.

Capillary Action

A convenient way of loading a liquid sample into a microfluidic system is by capillary action. A sample collection port is wetted with the sample and the sample is effectively drawn into the narrow, hydrophilic channels and chambers of the microfluidic system by capillary forces.

Anticoagulant

An anticoagulant is a substance that interferes with the ability of blood to clot. Administered as a therapeutic drug, an anticoagulant can, for example, help reduce or prevent the occurrence of potentially health- and/or life-threatening emboli or thrombi.

Anticoagulant Reversal Agent

An anticoagulant reversal agent can be administered as a therapeutic drug in order to reverse partially or fully the effect of an anticoagulant. Restoration of the capacity of the blood to clot can be life-saving, for example, a patient who takes an anticoagulant and is experiencing a severe injury can be treated with a reversal reagent for restoration of blood clotting capacity and prevention of excessive blood loss.

"Open" and "Closed" Devices

An "open" device has a channel to the outside from an interior chamber, allowing for direct access of blood into the chamber. A "closed" device has no exterior channels, and is filled before being sealed to the outside except for small holes associated with sensors, electrodes, LEDs, and other elements utilized in assessing clotting within the chamber. The 'open version' of the microfluidic system is designed so that the chip can be inserted into its packaging first, be heated up, but still be accessible (open). A sample can be loaded into the system through wetting of the side port, with the chip residing already in its packaging. The sample will be drawn into the chip by capillary forces.

The 'closed version' of the microfluidic system will not be accessible to the user after it is placed into its packaging. A sample has to be loaded into the system prior to placement of the chip into its packaging through wetting of or pipetting into one of the back side ports.

II. Device

Figure 10B:
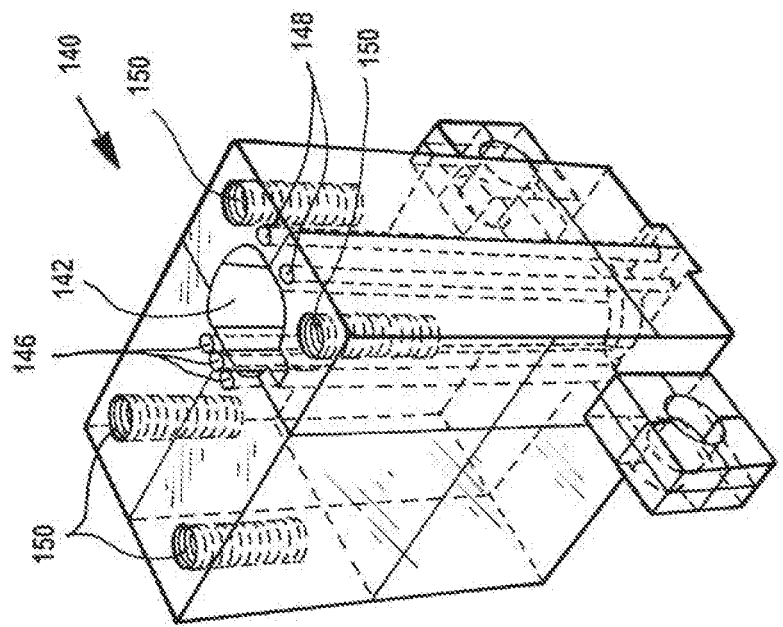
FIG. 10B is a perspective cross-sectional view from the side and top of the top of the open version reader.
Figure 10A:
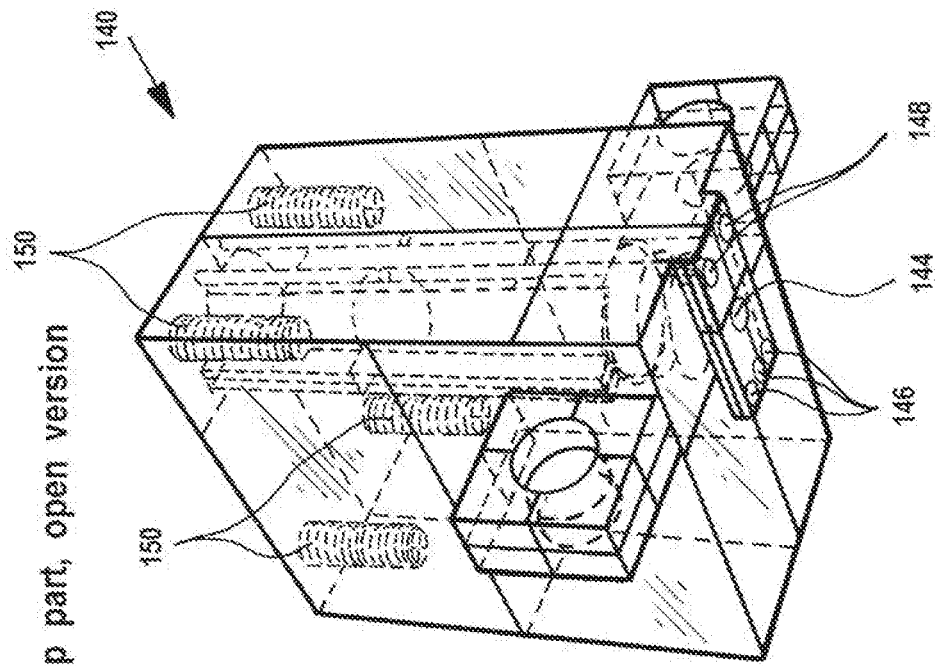
FIG. 10A is a perspective cross-sectional view from the side and bottom of the top of the open version reader.
Figure 11:
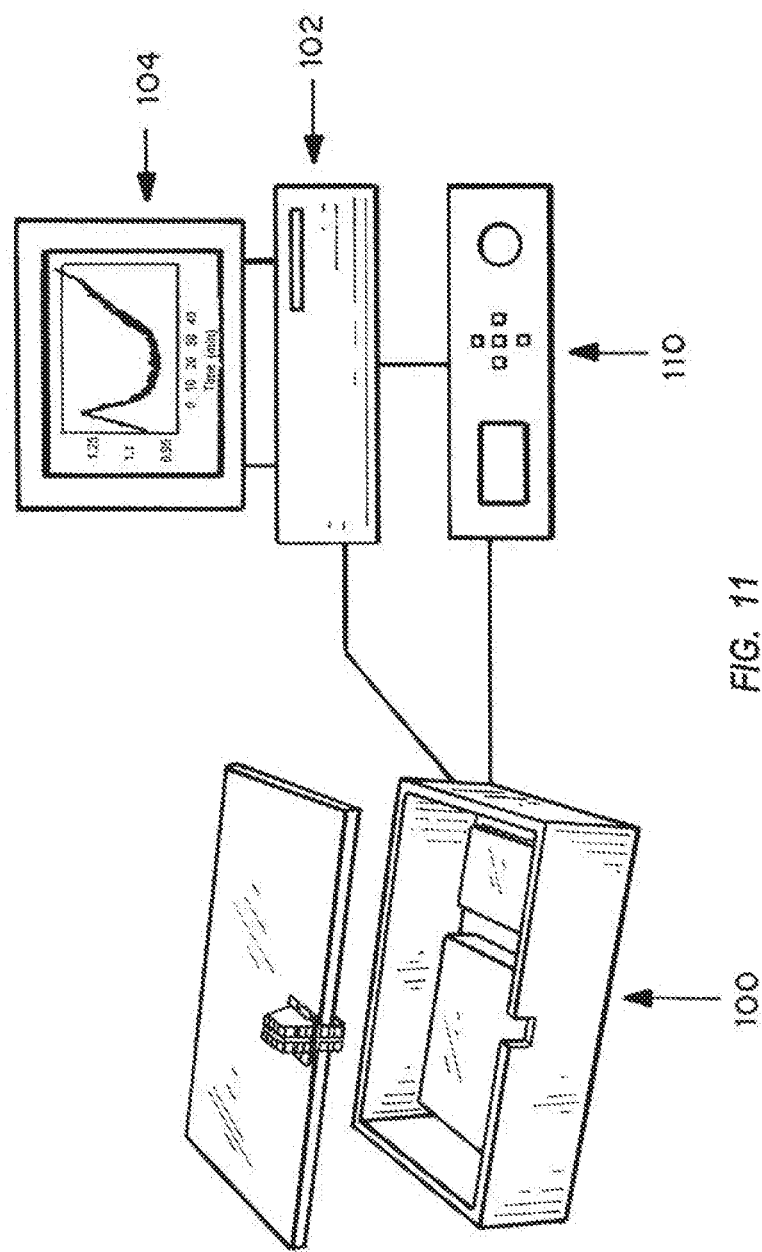
FIG. 11 is a schematic of the system, showing a box containing the single use disposable assay chambers, the reader, and the connections to a computer processor and monitor.
Figure 12A:
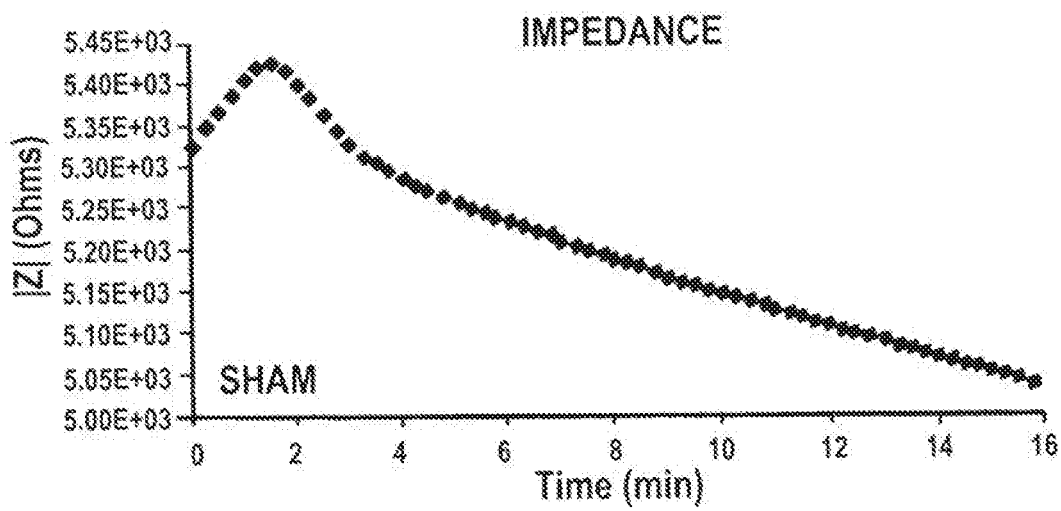
FIGS. 12A-12F are graphs of the impedance (12A, 12C, and 12E) and infrared transmission (12B, 12D, 12F) over time in minutes for control no anticoagulant, 300 ng edoxaban anticoagulant/ml blood, and 300 ng edoxaban and ciraparantag (PER977; an anticoagulant reversal agent)/ml of blood, respectively.
Figure 12B:
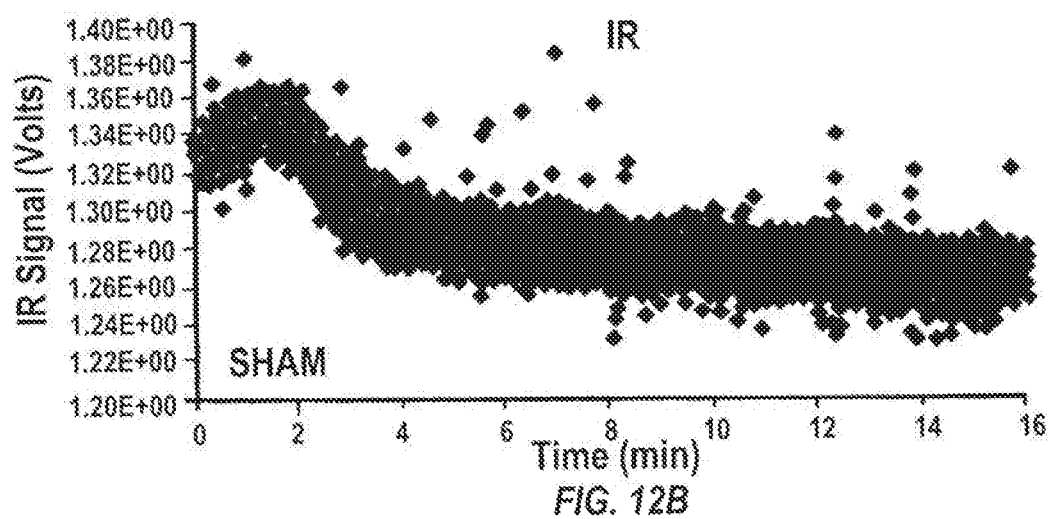
Figure 12C:
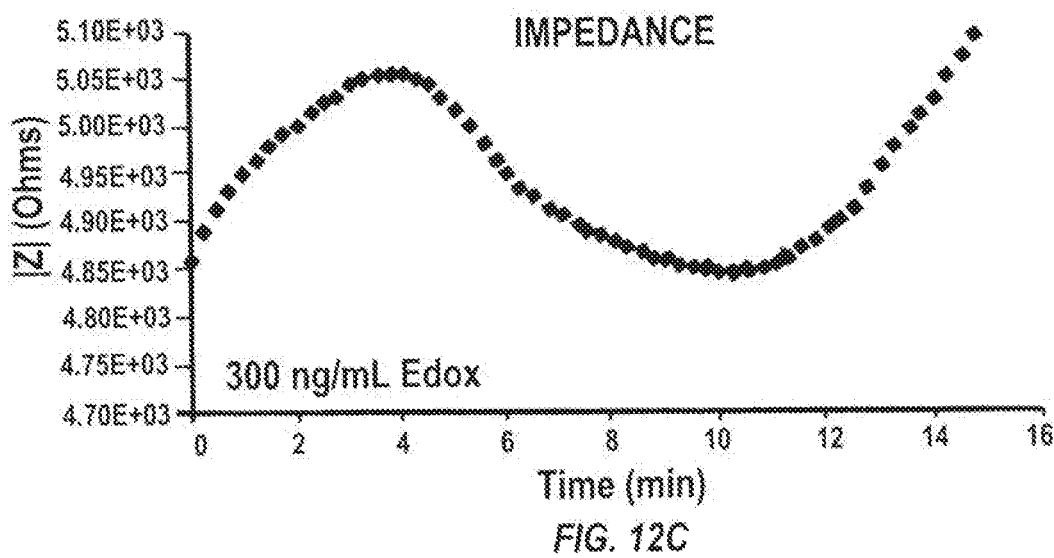
Figure 12D:
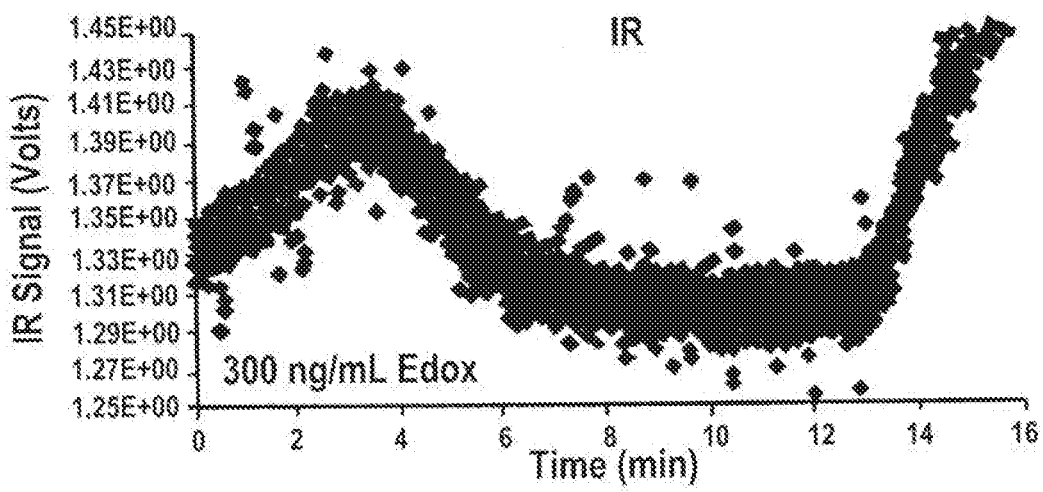
Figure 12E:
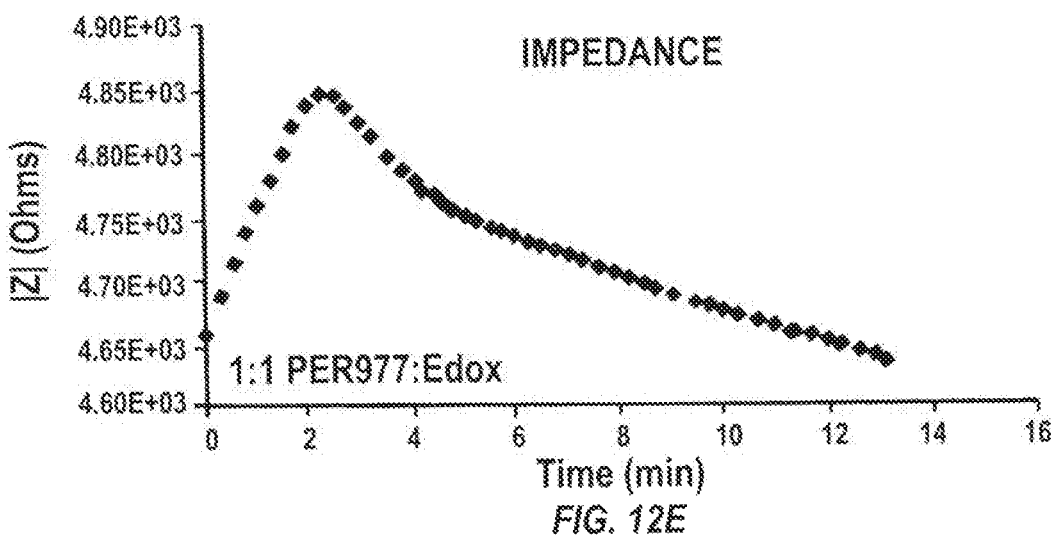
Figure 12F:
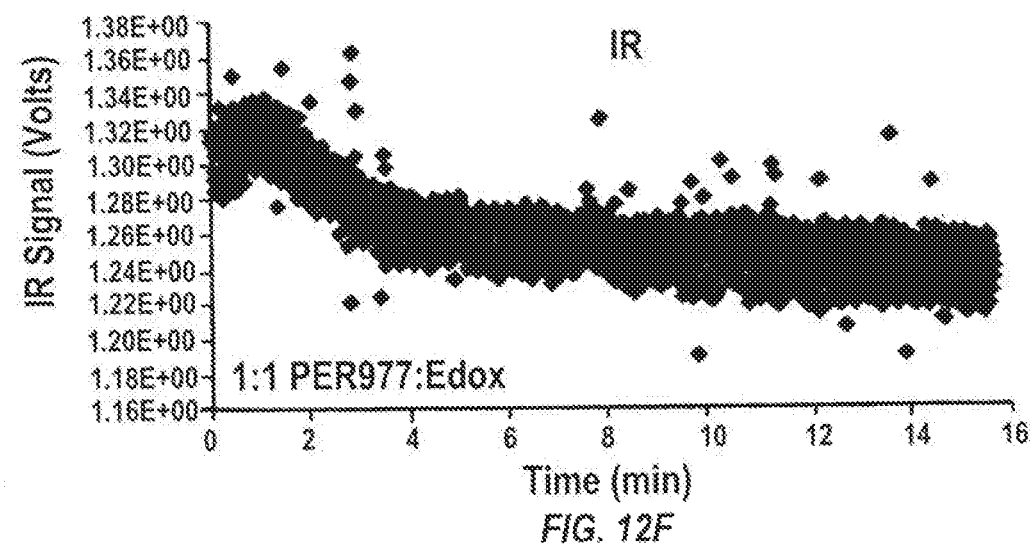

Embodiments of the microfluidic chip and its reader are shown in FIGS. 2-10, with the system including both parts reflected by FIG. 11. As indicated in FIGS. 2A and 2B, microfluidic chips 10 are fabricated through anisotropic wet etching of silicon wafers and subsequent thermal oxidation, isotropic wet etching of PYREX® (a clear, low-thermal-expansion borosilicate glass) wafers, sputter deposition of thin metal films onto both wafers through stencils, anodic bonding of silicon and PYREX® wafers, and subsequent separation of single chips by wafer dicing.

The microfluidic chips can be fabricated by alternative means, using any method that is suited to generate microfluidic structures and any negatively charged material that is suited to activate the blood clotting cascade.

The cross-sectional dimensions and geometries of the chambers 12a and 12b and the channel 14 connecting the chambers can be modified, and the number of chambers can be varied. The surface to volume ratio will overall influence the clotting time. Access to the chambers is direct ("closed", FIG. 2B), prior to sealing of the chamber device, or via a side channel 16 that allows access from the exterior of the microchambers.

Figure 3B:
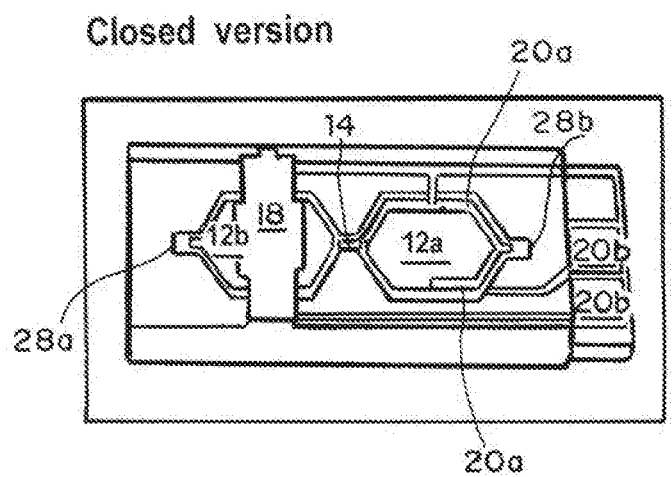
FIG. 3B is a view of the closed of the two sample chamber devices.
Figure 3A:
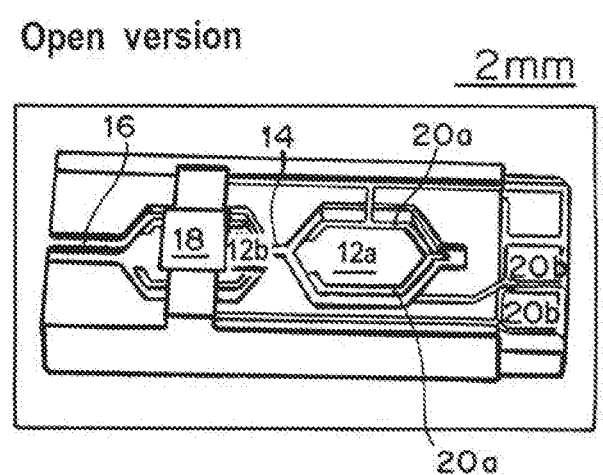
FIG. 3A is a view of the open version of the two sample chamber devices.
Figure 4B:
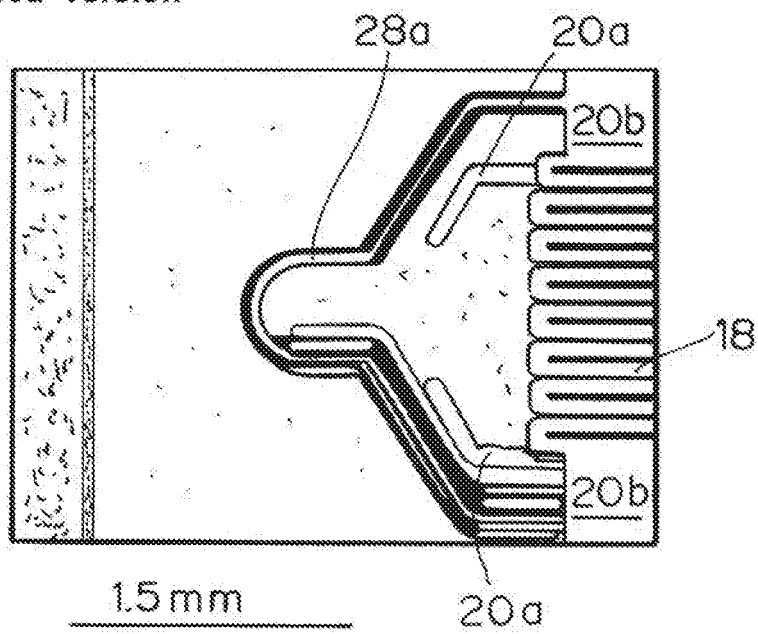
FIGS. 4A-4H are views of the chambers showing the chambers, connecting channels, electrical contact pads, and thermistors.
Figure 4A:
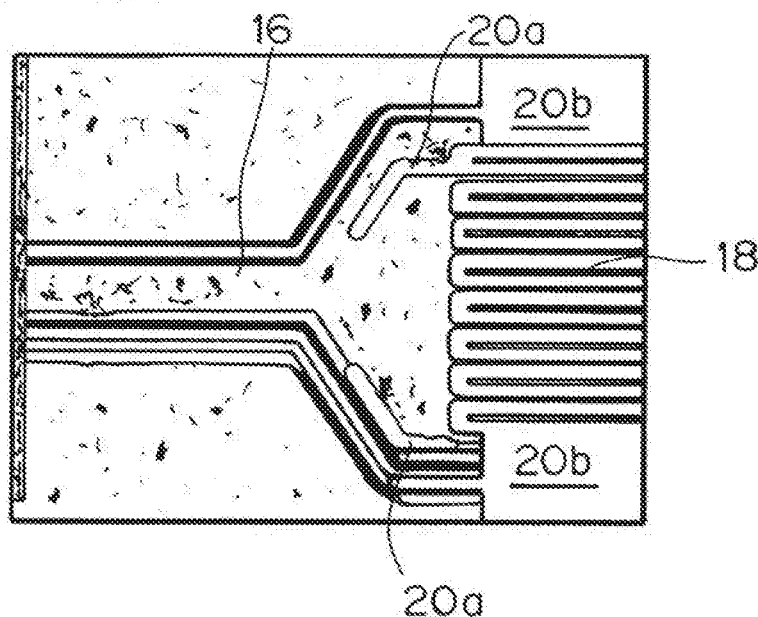
Figures 4C, 4D, 4E, 4F:
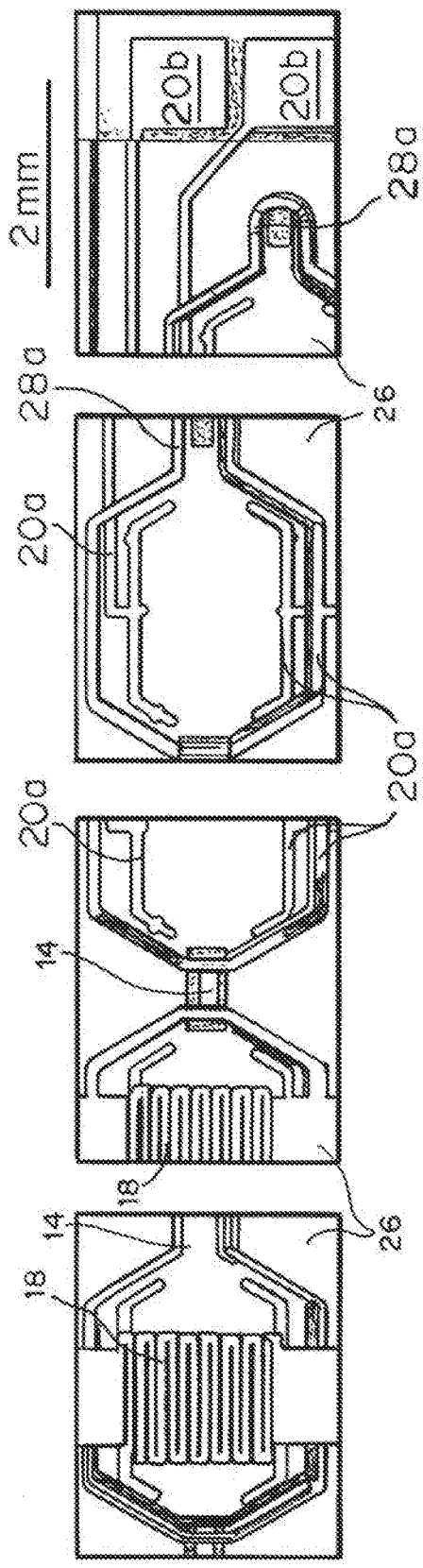
Figures 4G, 4H:
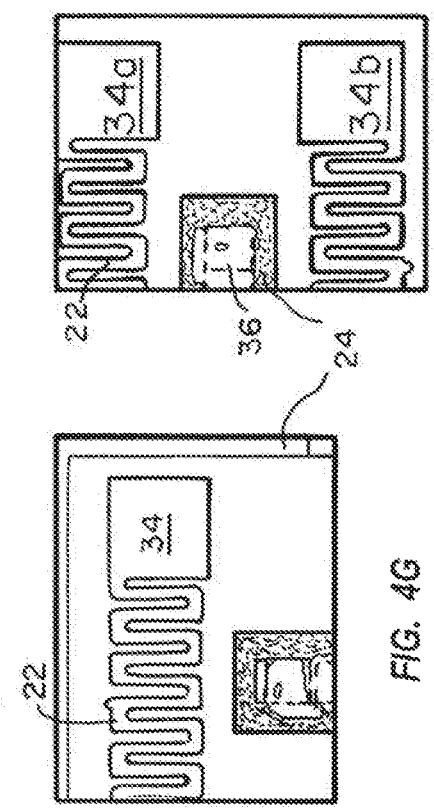

As shown by FIGS. 3A and 3B, the chips are designed to enable:

Heating through backside resistance or electrical heater structure (on underside of chambers 12a and 12b)
Temperature measurement for heating control through top side (outer) thermistor 18
Clotting detection through air pressure measurements
Clotting detection through measurement of impedance across blood sample through embedded electrodes 20a and contact pads 20b
Clotting detection through optical measurements As shown in FIGS. 4A-4H, resistance structures 22 are deposited onto the back of a silicon wafer 24 (to form resistive heating structures 32, FIGS. 4G, 4H), onto the front side 26 of the silicon wafer (to form electrodes 20a, 20b for impedance measurements and thermistors 18, respectively, at the floor of each chamber), and onto the front side of the PYREX® wafer (to form thermistors 18 on top of one or both chambers 12a, 12b). The heater and the thermistor can be external to the "chip", and can be integrated into the reader structure, if the walls of the cavity into which the chip is placed are of significantly greater mass than the chip, highly thermally conductive, and form an almost complete surround, then the cavity approximates a "black body" and the chip must come to thermal equilibrium with the cavity. If the chip is in contact with the cavity, or closely spaced, the equilibrium time constant can be very short. This can be established by pyrometer measurement during development. This should reduce the complexity of the disposable part of the system, and the cost. Connecting channel 14 and entry port 36 can be etched using potassium hydroxide (KOH) into the silicon wafer 26.

Figure 2A:
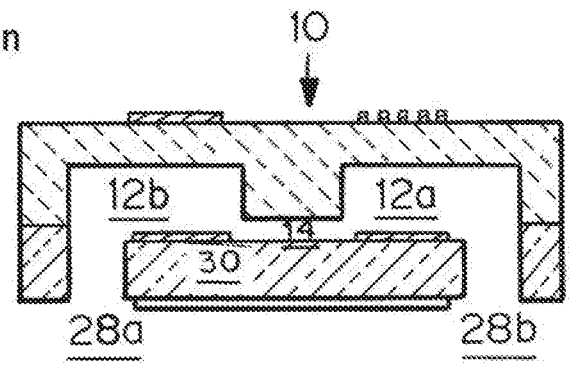
FIG. 2A is a cross-sectional view of one embodiment of the microfluidic device in which blood is pipetted into one chamber, and the chip is then inserted into packaging.
Figure 2B:
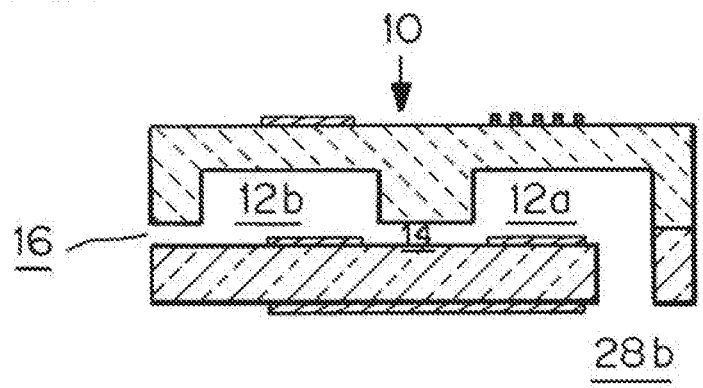
FIG. 2B is a cross-sectional view of an embodiment of the microfluidic device where blood can be introduced through chamber side; "sipper" sticks out of reader, similar to blood glucose measurement.

The device in FIG. 2B, 3B (called 'closed device') has two entry ports 28a, 28b etched through the silicon part 30. A sample can be pipetted into one of the ports 28a, 28b before the device 10 is inserted into a sealed packaging. The device in FIGS. 2a, 3b has one entry port 28b etched through the silicon part and one sideway entry port 16, realized as channel etched into the PYREX® (called 'open device'). In the cases of a silicon substrate, the surface wave structure can be directly integrated into the microfluidic design by well understood microfabrication techniques. An open device chip (FIGS. 2A, 3A) can be inserted into a sealed packaging and/or reader first, with the edge with the sideway port sticking out of the reader. Wetting of the sideway port 16 will then result in sample being drawn into the chamber 12a by capillary action.

The combined heater/cooler control system and the thermistor can be external to the 'chip', and can be integrated into the reader structure. If the walls of the cavity, into which the chip is place, are of significantly greater mass than the chip, highly thermally conductive, and form an almost complete surround, then the cavity approximates a 'black body' and the chip must come to thermal equilibrium with the cavity. If the chip is in contact with the cavity, or closely space, the equilibrium time constant can be very short. This can be established by pyrometer measurement during development. This would reduce the complexity of the disposable part of the system and (hopefully) the cost.

Chip packages or "readers" as shown in FIGS. 5-10, provide electrical, optical and fluidic interfaces to the chip. A reader consists of a bottom (FIGS. 5, 6, 9A, 9B) and a top (FIGS. 7, 8, 10A, 10B) part that are manufactured by high precision 3D printing, molding, machining, or other fabrication processes. Both parts are joined and pressed against each other by locking metal dowel pins that fit into holes 56. The reader can include means for display, storage of information, and a communications capability.

Figure 5:
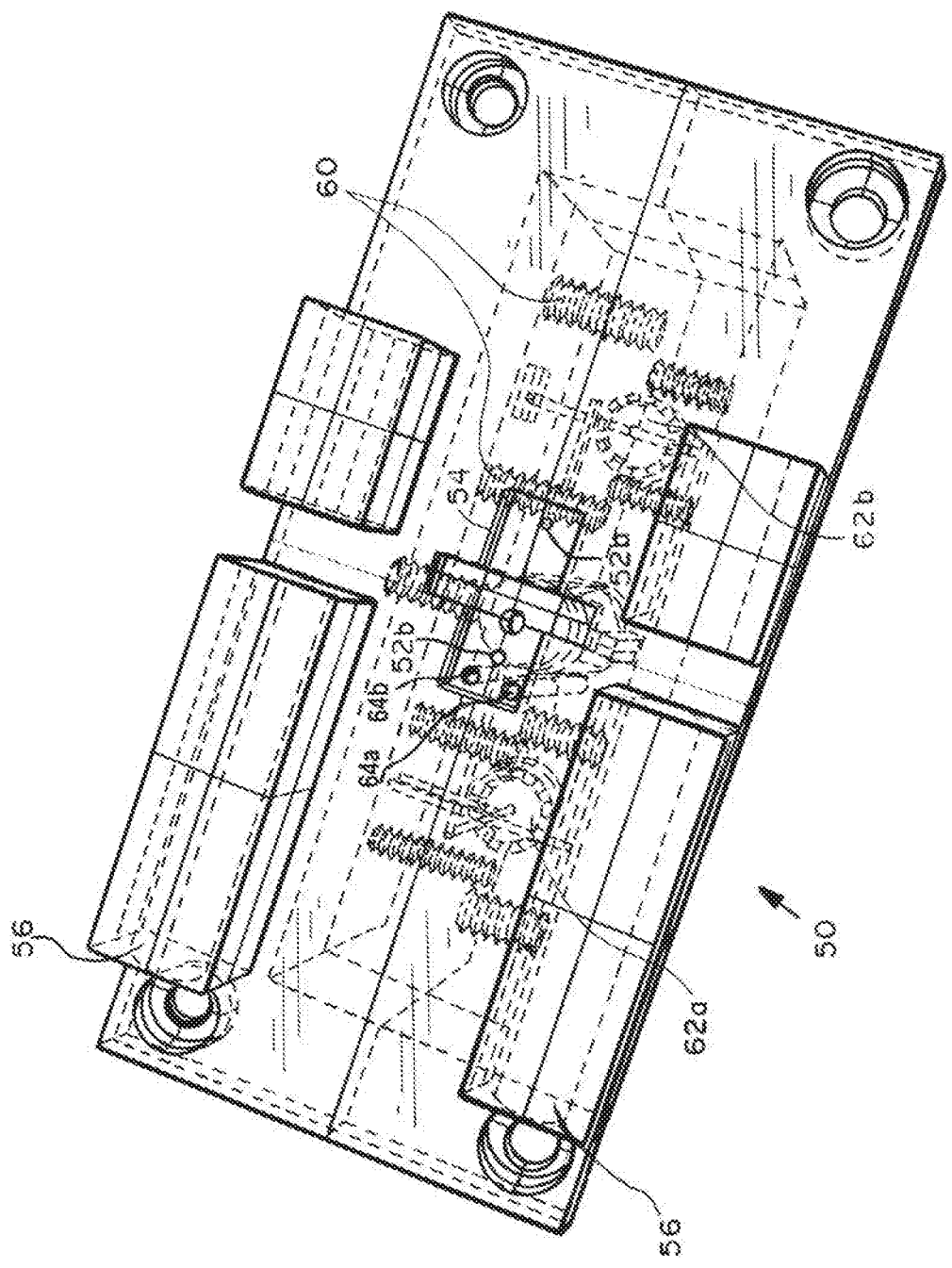
FIG. 5 is a perspective view from the top of the bottom of the closed version reader.
Figure 6:
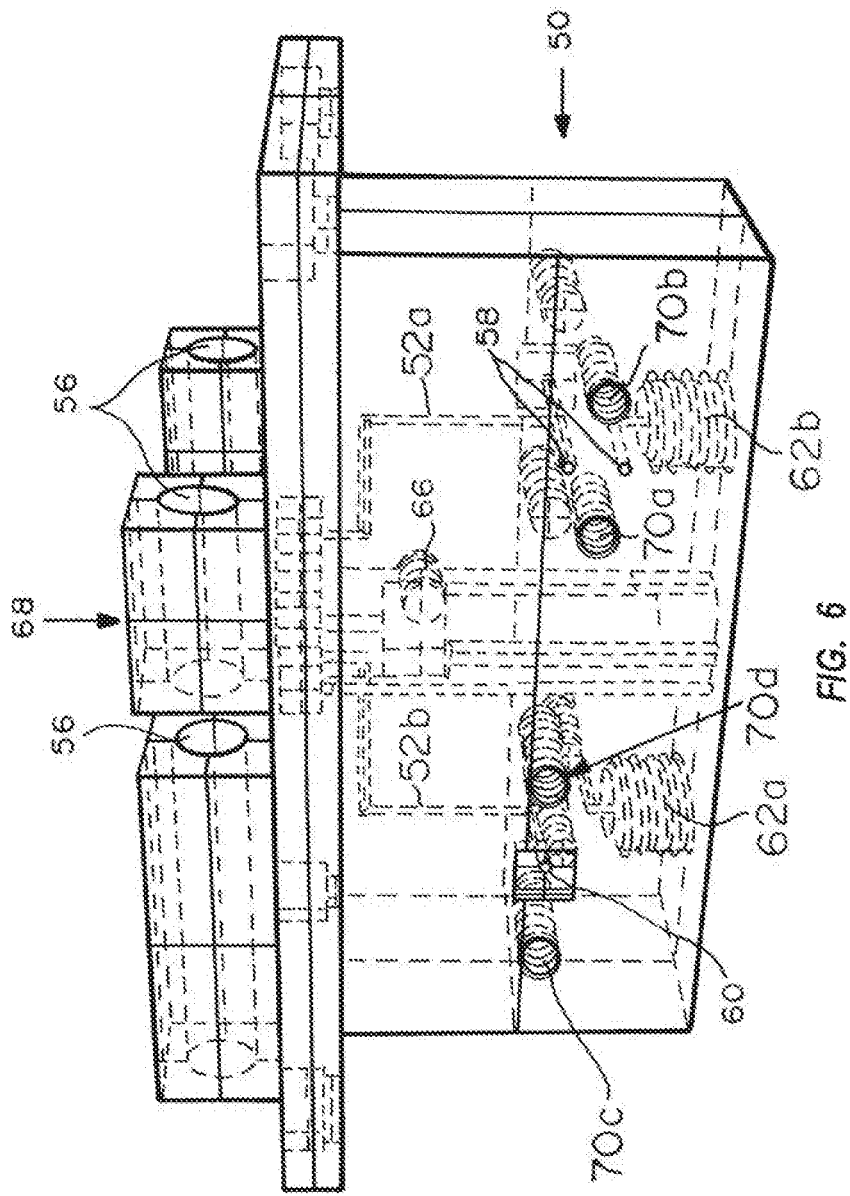
FIG. 6 is a cross-sectional view of the side of the bottom of the closed version reader.

FIGS. 5 and 6 show the bottom reader part 50 for the closed device chip from two different angles. Channels 52a, 52b, located in recess 54, inside the reader connect chambers 2 and 1, respectively, to the chip entry ports. On one side of the reader, a solenoid valve (not shown) can be attached to the reader at channel ends 58 to control the connection between the reader channel and a barbed tube connector that is screwed into the bottom of the reader. On the opposing side, a pressure sensor (not shown) can be attached to the reader at holes 60 to monitor the pressure applied to the reader channel and chip entry port. Each entry port 62a, 62b is controlled/monitored by its own solenoid valve/pressure sensor secured at holes 70a, 70b, 70c, and 70d. The bottom reader part exhibits a recess 54 for the microfluidic chip. Small vertical holes 64a, 64b hold pogo pins to contact the heater structure at the bottom of the chip. A hole 66 at the center of the reader part holds an IR LED chip in a metal can reader, which passes along light path 68.

The IR components can be molded or integrated into a "chipstrate" form.

Although shown as a single point optical measurement, a multipoint optical measurement could be used.

Figure 7:
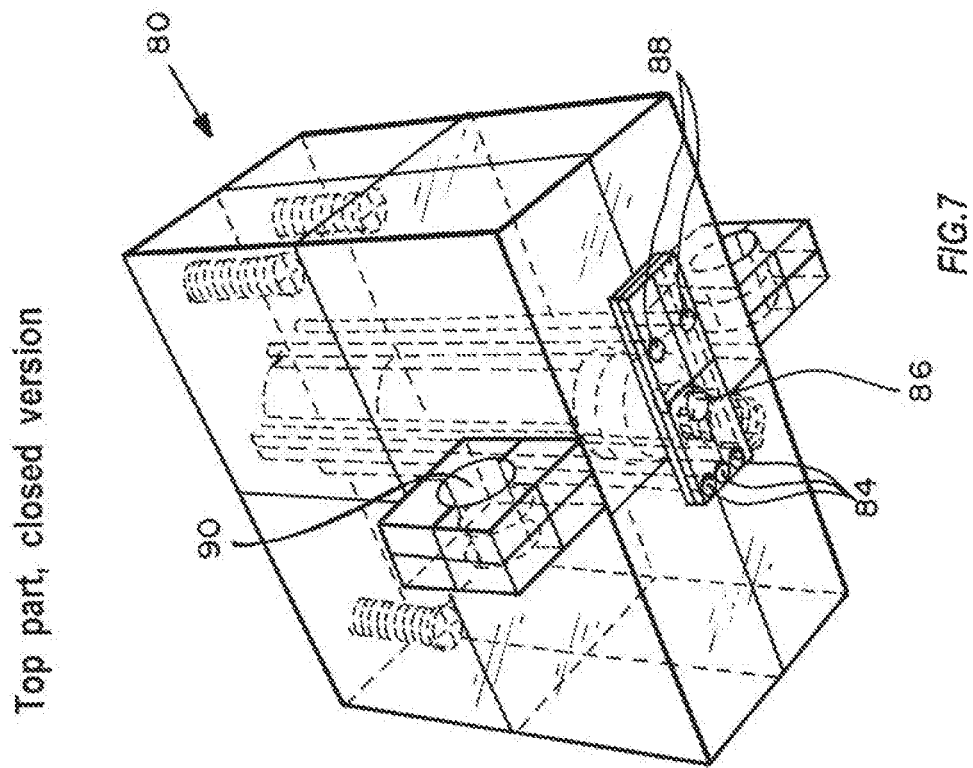
FIG. 7 is a perspective cross-sectional view of the top of the closed version reader showing the sample assaying device in place.
Figure 8:
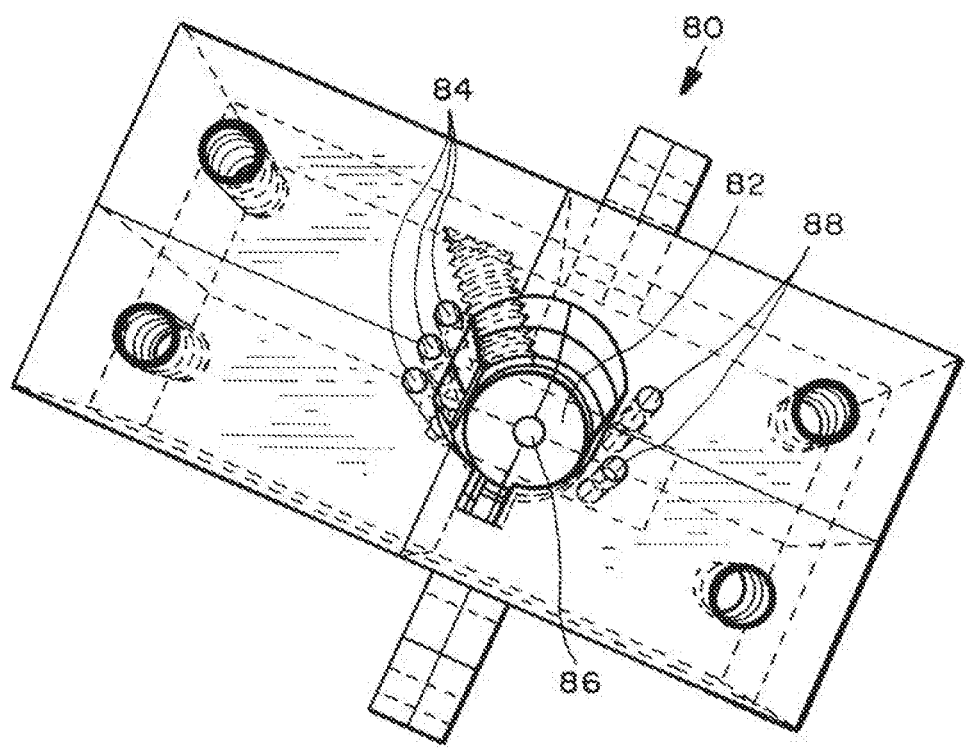
FIG. 8 is a perspective cross-sectional view from the top of the top of the closed version reader.

FIGS. 7 and 8 show the top reader part 80 for the closed device chip from two different angles. The large (for example, 5 mm) hole 82 in the center holds an IR photodiode chip (not shown) in a metal can reader that directs light through hole 86. Three small (for example, less than one mm) vertical holes 84 hold three pogo pins (not shown) to contact three electrodes for impedance measurements (one common ground electrode for both chambers and one counter electrode in each chamber), so that impedance measurements can be carried out in both chambers. Two other vertical holes 88 hold pogo pins to contact the thermistor on top of the chip. Other embodiments of these devices are known and readily available for the same function. IR LED and photodiode are placed so that they interrogate the 1 mm diameter center region of one chamber.

The chip reader itself is attached to the cover of a project box 100 that contains electronic circuitry, valves, and pumps needed to perform automated measurements, as shown in FIG. 11. The project box 100 is connected to a PC 102 where measurements are controlled by a LabView program and processor 110, and results shown on monitor 104.

Figure 9B:
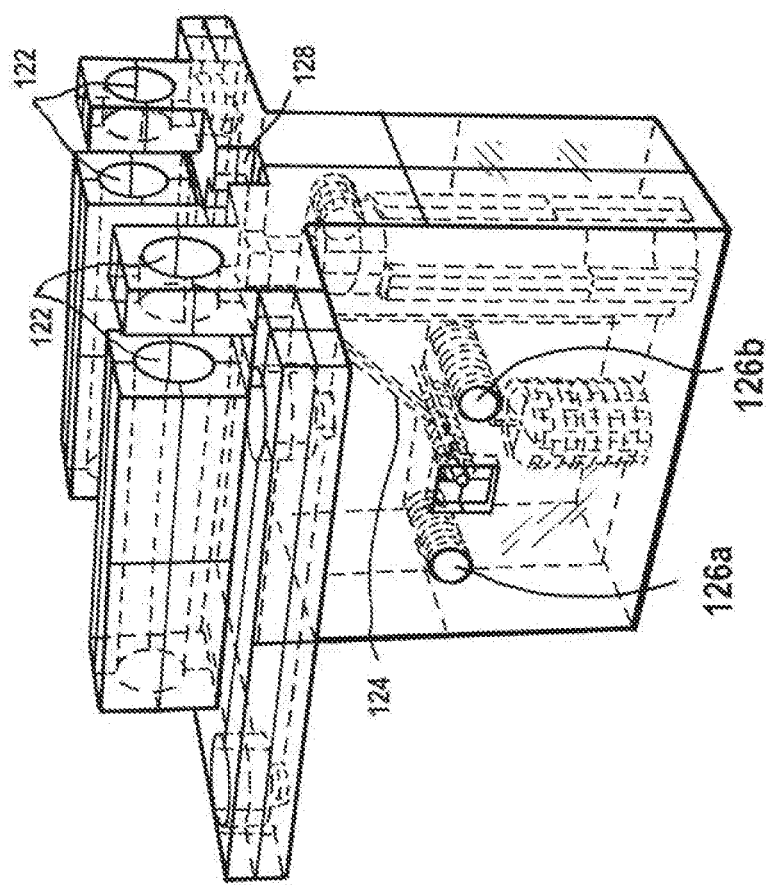
FIG. 9B is a perspective cross-sectional view from the side of the bottom part of the open version reader.
Figure 9A:
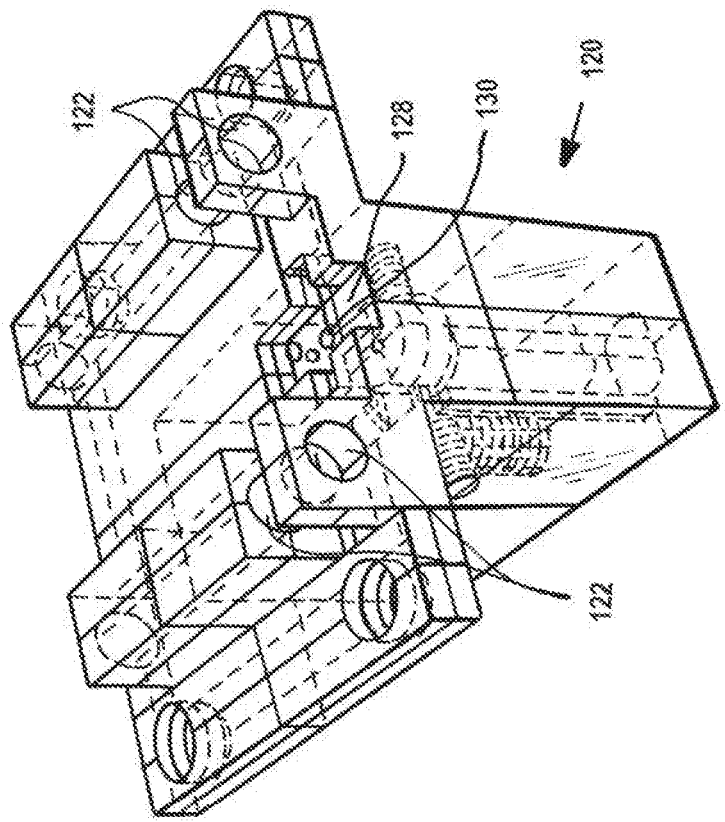
FIG. 9A is a perspective cross-sectional view from the top of the bottom part of the open version reader.

FIGS. 9A and 9B show the bottom reader part 120 for the open device chip from two different angles. Dowel pin holes 122 are used to secure the device. Channels 124 inside the reader connect chambers 2 and 1, respectively, to the chip entry ports. On one side of the reader, a solenoid valve (not shown) can be attached to the reader at channel ends to control the connection between the reader channel and a barbed tube connector that is screwed into the bottom of the reader. On the opposing side, a pressure sensor (not shown) can be attached to the reader at holes 126a, 126b to monitor the pressure applied to the reader channel and chip entry port. Each entry port is controlled/monitored by its own solenoid valve/pressure sensor secured at holes. The bottom reader part exhibits a recess 128 for the microfluidic chip. A hole 130 at the center of the reader part holds an IR LED chip in a metal can reader.

FIGS. 10A and 10B show the top reader part 140 for the open device chip from two different angles. The large (for example, 5 mm) hole 142 in the center holds an IR photodiode chip (not shown) in a metal can reader that directs light through hole 144. Three small (for example, less than one mm) vertical holes 146 hold three pogo pins (not shown) to contact three electrodes for impedance measurements (one common ground electrode for both chambers and one counter electrode in each chamber), so that impedance measurements can be carried out in both chambers. Two other vertical holes 148 hold pogo pins to contact the thermistor on top of the chip. IR LED and photodiode are placed so that they interrogate the 1 mm diameter center region of one chamber.

Although described with reference to interrogation of both chambers with one beam, it is possible to interrogate both chambers using separate beams. One beam is shown for illustration purposes only.

The chip reader is attached to the cover plate of a project box as described above using screw holes 150, as shown in FIG. 11.

A. Surfaces for Activation of Blood Clotting

The microfluidic system is fabricated so that the introduced blood or plasma sample is in contact with a glass surface, the top part of the microfluidic chip and/or the surface of the bottom part of the microfluidic chip, formed of a material such as PYREX® or thermally oxidized silicon, such as amorphous $SiO_2$, silicon oxide, and silicon nitride. The glass serves to activate the clotting cascade without use of additional chemical or biological reagents. Activation is either achieved through mere contact of the sample with the glass surface or through active movement (for example, through an externally applied air pressure pulse) of the sample along the glass surfaces inside the microfluidic system.

The microfluidic system is fabricated so that the introduced blood or plasma sample is in contact with glass surfaces (or other negatively charged surfaces), which serve to activate the clotting cascade without use of additional chemical or biological reagents. Glass surfaces are generated through use of glass wafers and oxidized silicon wafers, respectively, for fabrication of microfluidic systems. Alternatively, glass surfaces can be realized through use of glass chips that are integrated in reader parts that form a microfluidic system, through deposition of glass onto the inner surfaces of the microfluidic system (for example, through use of spin-on glass products) or through integration of small objects with glass surfaces (for example, glass microbeads) inside the microfluidic system. Additionally glass surfaces can be introduced by the oxidation of silicon surfaces.

B. Electrical Characteristics of Deposited Metal Thin Films

Deposited metal thin films can be formed of chromium adhesion layers (approximately 20 nm thick) and gold top layers (approximately 50 nm thick for inner electrodes for impedance measurements, 100 nm thick for thermistors and 150 nm thick for heater structures). Spring-loaded pogo pins in the plastic reader were used to realize electrical contacts to all thin film electrodes on the microfluidic chip. Typical resistances between two pins connected to either end of a metal film test structure, with approximate length of 2 mm and width of 1 mm, are 1.8 Ohm, with pins contacting metal films for heater structures, 2.7 Ohm, contacting metal films for thermistors, and 22 Ohm, contacting metal films for inner electrodes for impedance measurements. The markedly higher resistance between inner electrode pins is likely due to a thinner gold layer and possibly contact degradation during anodic bonding at approximately 300° C. Heater structures and thermistors are deposited after anodic bonding.

For measurement of temperature coefficients of resistances of deposited metal thin films, a chip was used that exhibited resistor/thermistor structures instead of open circuit electrodes for impedance measurements. The chip was inserted into its reader and heated up inside an oven. Electrical resistances of heater, thermistor and inner electrode resistors were measured at different temperatures and temperature coefficients of resistances a were calculated:

heater thin film: $\alpha=0.0016$ $K^{-1}$
thermistors thin film: $\alpha=0.00115$ $K^{-1}$
inner electrode thin film: $\alpha=0.000108$ $K^{-1}$.

C. Internal Electrodes for Sample Positioning

Apart from impedance measurements, integrated electrodes can also be used to detect the presence of the analyte, such as fibrin, in the microfluidic system and/or to track movement of the analyte, for example, due to externally applied air pressure pulses. Such detection and tracking can be used to initiate the analysis procedure once the analyte is added to the microfluidic system, to position the analyte at a specific location within the microfluidic system, and to move it repeatedly back and forth between defined locations, respectively.

Although exemplified with reference to two chambers and two electrodes, multiple electrodes can be used to confirm filling of multiple chambers, at the site of measurement of clotting or at a point prior to the chamber where the clotting is measurement, such as closer to the inlet.

Repeated movement of whole blood or blood plasma along glass surfaces can be applied to increase activation of the blood, to accelerate blood clotting and/or to decrease measurement times.

D. Integration of Filter Structures

Mechanical filter structures can be integrated into the microfluidic chip, so that only blood plasma is arriving at the analysis chambers. The filters can be realized as array of micropillars or as microchannels etched into silicon or glass. This way, plasma (without the use of an anticoagulant such as sodium citrate or EDTA) can be produced in situ and very quickly tested in the same manner as whole blood, without red blood cell interference in the analysis. The micropillar arrays can be arranged in offset patterns to inhibit red blood cell transit, while minimizing the probability of "plugging" an excessive fraction of the available channel cross section.

E. Means for Clotting Detection

A variety of modalities can be applied to determine blood clotting times.

Viscosity

The viscosity of the blood can serve as a measure to characterize clotting times. Two general principles may be applied to yield a direct or indirect measure for the viscosity. The sample can be moved through a channel with known geometry. Viscosity can be measured by tracking the rate of penetration through a "long" channel either optically or by imaging or multiple beam "check points" or electrically by multiple electrode impedance sensors. The viscosity may be measured indirectly, for example through measurement of the distance the sample has travelled inside a channel during a specific time interval, the sample volume that has been displaced during a specific time internal, or the change in driving force during a specific time interval (for example, if the sample is moved by a pressurized volume of trapped air, the change in air pressure can serve as an indirect measure for sample volume displacement). Alternatively, objects can be moved through the blood sample, for example, driven through electrostatic or magnetic forces. Tracking of the object movement can yield an indirect measure for the sample viscosity.

The viscosity of the analyte can be detected through movement of the analyte inside the microfluidic system through a pressurized, entrapped air volume. Air can be pressurized, for example, through electric air pumps that are connected to the microfluidic system. Pressurized air can be entrapped through closure of solenoid valves connected to the microfluidic system. Decreasing pressure of the entrapped air at one entry port of the chip indicates movement of the analyte. Knowledge of the geometry of the microfluidic system and the magnitude of the applied pressure allows calculation of analyte viscosity and detection of viscosity changes (for example, a viscosity increase due to clotting in case of blood).

Clot detection by viscosity monitoring involves measuring differential pressure across an on-chip inlet and outlet, connected to fluidic ports on the reader (made air/fluid tight using o-ring seals).

The viscosity of the analyte can be detected through movement of the analyte inside the microfluidic system through a pressurized, entrapped air volume. Air can be pressurized, for example, through electric air pumps that are connected to the microfluidic system. Pressurized air can be entrapped through closure of solenoid valves connected to the microfluidic system. Decreasing pressure of the entrapped air at one entry port of the chip indicates movement of the analyte. Knowledge of the geometry of the microfluidic system and the magnitude of the applied pressure allows calculation of analyte viscosity and detection of viscosity changes (for example, a viscosity increase due to clotting in case of blood).

Impedance

Clotting of a sample can be related to its electrical impedance, or its complex resistance when an electric current or voltage is applied. The electrical impedance results from ohmic resistances as well as capacitive components of the sample. The electrical impedance can, for example, be measured through electrodes that are directly integrated in the microfluidic chip or integrated in the reader that forms, together with other parts, a microfluidic system. Electrodes can be partially in direct contact with the sample or separated from the sample only through a thin insulator (with a thickness ranging from nanometers up to hundreds of micrometers).

Electrodes and conductor lines may be formed as patterned thin metal films that are deposited onto substrates forming the microfluidic system. Electrodes and conductor lines can also be realized through integration of patterned metal sheets or films that are inserted and sandwiched between reader parts. If semiconductor wafers are used to fabricate microfluidic chips, the semiconductor material itself can contain integrated electrodes fabricated by diffusion, implantation, etching, micro machining, or any combination of appropriate techniques similar to the techniques used in integrated circuit or other micro device production. The integrated electrodes can be used to measure directly electrical properties of the analyte (for example, resistance, capacitance, impedance). Suitable electronic circuits may also be used to translate analyte changes (and related changes in electrical properties) into measureable electric voltages, currents, frequencies or other suitable parameters. Parts can also be inserted during construction by 3D printing, or integrated directly. For example, a resistor heating element would be fabricated by a doped channel in a semiconductor substrate (by ion beam implantation, for example).

Clot detection by impedance monitoring is accomplished by inserting the chip into the reader, making contact between gold pads (connected to the on-chip electrodes) and Pogo pins in the reader from which the electrical signal is read by an LCR meter, for example, or any other appropriate measurement system.

For detection of clotting through measurement of impedances, a sample is loaded into the chip, the chip is inserted into its reader, and the pogo pins connecting to the internal impedance electrodes connected via Kelvin clip leads to a QuadTech 1920 LCR meter. The magnitude and the phase of the complex impedance of the blood sample were recorded at 15 second intervals. Measurements at 100 Hz, 1 kHz, 10 kHz, and 100 kHz showed characteristics peaks or plateaus of either the magnitude or the phase or both. The peaks or plateaus indicated a measure for the clotting time.

Referring to FIGS. 3A-3B, for impedance measurements, the external LCR meter applies an AC voltage (20 mV RMS) between the two electrodes 20b, 20a on each side of the chamber 12a, and measures the electrical current between the electrodes. The magnitude and phase of impedance are then computed and the clotting calculated.

Optical Properties

Optical properties of the sample can be related to clotting events. Light with wavelength in the range of 500 nm to 10,000 nm (preferably 1,300 nm) can be used to illuminate the sample through the microfluidic and chip reader. The following parameters can be used to track clotting: transmitted, reflected and scattered light. If a coherent light source is used, polarization may be used as additional parameter.

Clot detection by IR transmission is performed by inserting the chip into the reader and measuring infrared transmission across the thickness of the chip (through the glass, fluid-fill chamber, and underlying silicon). This is accomplished via placement of an IR source (LED) above the chip and photodiode detector aligned immediately below.

For optical clot detection, IR LED and photodiode are inserted into their reader parts as described above. A blood sample is pipetted into the chip and the chip placed into the reader. The sample is continuously illuminated with IR light at 1,300 nm. At time intervals of typically 100 ms, the voltage drop across a 1 MOhm resistor caused by the photocurrent of the photodiode was recorded. Voltages typically measured several volts. Clotting of the sample caused the transmitted light and the photocurrent to vary over time. Characteristic peaks of the transmitted light curve indicated a measure for the clotting time.

The continuous illumination measurement is presented as a simple illustration. More sophisticated measurement techniques may be used. For example, if the IR emitter were illuminated for 50% duration, at a repetition rate of 1 khz, and a synchronous detector were used to process the photodetector output, followed by a 1 second integration period, the signal to noise ratio in the above example could be improved by as much as thirty-fold. In addition, active signal processing would allow processing of much smaller signals, permitting a relatively low impedance termination of the photodetector, lowering the intrinsic noise, and canceling drift. Ambient electrical noise sensitivity would be substantially reduced.

Acoustic Properties

Measurement of sound propagation in the sample or along the sample surface can serve as an additional measure for clotting. External ultrasound transducers can be used to measure the time it takes ultrasound to travel through the sample. Additionally, surface acoustic wave devices can be used to measure acoustic properties of the sample and to detect clotting.

III. Methods of Making Devices

In addition to standard processes such as photolithography, special technologies such as anodic bonding or potassium hydroxide anisotropic wet etching of silicon wafers can be applied to form microsystems. Apart from standard ultraviolet light lithography, techniques such as direct laser writing microablation or erosion, electron beam lithography, or focused ion beam milling can be used to define micro- or nanometer-sized structures. Soft lithography is a related way to fabricate microfluidic systems and is based on generation of microstructures or -patterns, for example, through standard photolithography techniques, and subsequent use of these patterns in molding/casting processes. Elastomeric material such as polydimethylsiloxane (PDMS) are typically used for generation of microfluidic system by soft lithography. Structured films generated by soft lithography can be attached to each other or to any other structured or non-structured substrate to form complex microfluidic systems. Furthermore, other technologies such as drilling, milling, molding, or 3D printing, may be used alone or in combination with other micro-/nanotechnologies to fabricate microsystems.

IV. Sample Collection

Blood Collection

In most cases, individuals to be tested will present at a clinic or a hospital, possibly with unknown status as to treatment with anticoagulants. Blood can be obtained by the use of a syringe, a lancelet, or directly from a blood containing line. Due to the use of the alternative clotting pathway in which clotting is activated using a glass type surface, the blood may contain anticoagulants such as warfarin, heparin, low molecular weight heparin, factor IIa inhibitors, factor Xa inhibitors, and other factor inhibiting or factor impaired blood.

Warfarin and related 4-hydroxycoumarin-containing molecules decrease blood coagulation by inhibiting vitamin K epoxide reductase, an enzyme that recycles oxidized vitamin $K_1$ to its reduced form after it has participated in the carboxylation of several blood coagulation proteins, mainly prothrombin and factor VII. Warfarin does not antagonize the action of vitamin but rather antagonizes vitamin $K_1$ recycling, depleting active vitamin K. Thus, the pharmacologic action may always be reversed by fresh vitamin K. When administered, these drugs do not anticoagulate blood immediately. Instead, onset of their effect requires about a day before remaining active clotting factors have had time to naturally disappear in metabolism, and the duration of action of a single dose of warfarin is 2 to 5 days. Reversal of warfarin's effect when it is discontinued or vitamin $K_1$ is administered, requires a similar time.

Heparin is a compound occurring in the liver and other tissues that inhibits blood coagulation. A sulfur-containing polysaccharide, it is used as an anticoagulant in the treatment of thrombosis. Low molecular weight heparin, a more highly processed product, is useful as it does not require monitoring by aPTT coagulation parameter (it has more predictable plasma levels) and has fewer side effects. However, in emergency bleeding situations the ability to monitor LMWH is a significant unmet clinical need as no point of care assay is clinically accepted for LMWH anticoagulant monitoring.

Drugs such as rivaroxaban, apixaban and edoxaban work by inhibiting factor Xa directly (unlike the heparins and fondaparinux, which work via antithrombin activation).

Another type of anticoagulant is the direct thrombin inhibitor. Current members of this class include the bivalent drugs hirudin, lepirudin, and bivalirudin; and the monovalent drugs argatroban and dabigatran.

The sample can be tested as blood or as plasma. Plasma can be prepared by filtration or centrifugation. Additionally, additional glass surface area can be added to one or more of the microfluidic channels by the introduction of glass beads into the channel using for example a double depth chip or in-channel bead packing.

Other Biological Samples

The device can be used with other types of samples that are activated with exposure to glass.

V. Methods of Use

The samples are collected and administered into the device. The means for determining clotting are started as the sample is placed into the device. Results are compared to standard results for uncoagulated samples, typically from pooled plasma or pooled blood, or by reference to the clotting time at initiation of treatment, as in the case where an individual is administered anticoagulant, or a therapeutic to neutralize the anticoagulant and restore more normal blood clotting.

The present invention will be further understood by reference to the following non-limiting examples.

Example 1. Demonstration of On-Chip Heating

A chip was used to demonstrate the effect of the integrated heater (or integrated heater/cooler; preferably a solid state heat pump or 'Peltier cooler') structure. A 12 V DC voltage was applied to the heater resistor on the back of the silicon part of the microfluidic chip. Resistances of thermistors were measured inside each chamber (inner thermistors, on the front silicon surface) and on top of each chamber (outer thermistors, on top of the PYREX®) before application of a heater voltage and during heating. Local temperatures increase due to heating were calculated using measured resistances and temperature coefficients of resistances as reported earlier. Room temperature was approximately 27° C. Average local temperature increases after approx. 2 min of unregulated heating were:
outer thermistors: ΔT=20.3 K
inner thermistors: ΔT=23.8 K.

Example 2. Measurement of Blood Clotting

Materials and Methods

Blood was harvested from a patient using commercially available lancing devices. 10 µL of blood were obtained and pipetted into an Eppendorf tube. Saline was used as a buffer solution. The blood sample was mixed in the Eppendorf tube through up and down pipetting five times with one of the following reagents:
1 µL of buffer solution (called sham control),
1 µL of buffer solution containing the anticoagulant edoxaban at a concentration of 300 ng/mL,
1 µL of buffer solution containing the anticoagulant edoxaban and the anticoagulant reversal agent PER977, both at a concentration of 300 ng/mL.

Edoxaban is a commercially available anticoagulant. PER977 (ciraparantag) is an investigational drug that is designed to reverse the effect of edoxaban. Immediately after mixing, 2.5 µL of each blood sample was pipetted into a closed device chip. The chip was inserted into its reader, and both IR light and impedance measurements were immediately recorded at room temperature (approximately 27° C.). Heating of the blood sample were omitted.

Results were obtained both by IR and viscosity impedance.

Results

As evident from FIGS. 12A-12F, IR (FIGS. 12B, 12D, and 12F) and impedance measurements (12A, 12C, and 12E) correlate well with each other. Both measurements show for the sham control a characteristic peak around 2 minutes that is indicative of the sample clotting time. Addition of the anticoagulant edoxaban shifts this peak to approximately 4 minutes. In addition to the peak, the edoxaban curves show a characteristic local minimum around 12 minutes. Addition of the anticoagulant reversal agent PER977 to a blood sample containing edoxaban shifts the peak in each curve back to 2 minutes and suppresses the occurrence of a local minimum around 12 minutes. These measurements indicate the clotting-delaying effect of edoxaban and the reversal of this effect through additional administration of PER977.

Modifications and variations of the devices, systems and methods of use thereof will be evident to those skilled in the art from the foregoing detailed description and are intended to come within the scope of the appended claims.

We claim:

1. A test microchip for measurement of clotting time in a blood or plasma sample, the test microchip comprising
an inlet for a blood or plasma sample, the inlet communicating with one or more microchannels having a length between tens of microns and millimeters,
each microchannel comprising one or more test chambers, each microchannel having a defined volume between nanoliters and milliliters and configured to draw the blood or plasma sample into the one or more test chambers by passive capillary action,
the one or more microchannels each comprising at least one anionically charged surface at the inlet into the microchannel and/or the entry into the test chamber which activates clotting of the blood or plasma sample upon entry of the blood or plasma sample into the one or more microchannels or test chamber,
wherein the anionically charged surface does not include chemical agents activating clotting, and
wherein changes in viscosity, impedance, acoustic properties, or optical properties indicative of clot formation can be measured in the test chamber.

2. The test microchip of claim 1 wherein the test chamber is formed of a material which allows changes in viscosity, impedance, acoustic properties, or optical properties in the blood or plasma in the test chamber.

3. The test microchip of claim 1 further comprising a temperature controlling element.

4. The test microchip of claim 1 further comprising electrical means for conveying the results of the change in viscosity, impedance, acoustic properties, or optical properties, to an external reader or monitor.

5. The test microchip of claim 1 fabricated through anisotropic wet etching of silicon wafers and subsequent thermal oxidation, isotropic wet etching of clear, low-thermal-expansion borosilicate glass wafers, sputter deposition of thin metal films onto wafers through stencils, anodic bonding of silicon and clear, low-thermal-expansion borosilicate glass wafers, or germanium or gallium and subsequent separation of single chips by wafer dicing.

6. The test microchip of claim 1 further comprising an IR LED or photodiode for measuring optical changes.

7. The test microchip of claim 1 comprising electrodes and conductor lines realized through integration of patterned metal sheets or films.

8. The test microchip of claim 1 comprising semiconductor material wherein the semiconductor material can serve as an electrode, and can be used to directly measure electrical properties of the analyte such as resistance, capacitance, and impedance.

9. The test microchip of claim 1 comprising a doped semiconductor substrate fabricated into a resistor heating element.

10. The test microchip of claim 1 wherein the test microchip comprises a single microchannel for measuring clotting.

11. The test microchip of claim 1 wherein the charged surface is glass and/or oxidized silicon.

12. The test microchip of claim 1 wherein each one or more test chambers is between one and ten microliters in volume.

13. The test microchip of claim 1 wherein the test microchip is single use.

14. A method for measuring clotting time comprising applying a blood or plasma sample to
the test microchip of claim 1 in a reader for measuring clotting in the blood or plasma sample,
wherein the reader comprises
a detector which determines changes in viscosity, impedance, acoustic properties, or optical properties in the blood or plasma sample in the test chamber to measure clotting time, and
a temperature control regulating the temperature of the test chamber,
wherein the detector is configured to output the measured clotting time determined from the time of activation of the blood or plasma sample to the time of the change in viscosity, impedance, acoustic properties, or optical properties in the test chamber indicative of clotting, and
obtaining output of the clotting time.

15. The method of claim 14 wherein the sample is from a person with anticoagulated blood.

16. The method of claim 15 wherein the type of anticoagulation is unknown.

17. The method of claim 14 wherein the blood is anticoagulated with an anticoagulant that affects blood so that clotting time cannot be measured with activated Partial Thromboplastin Time (aPTT).

* * * * *